United States Patent
Zimmer (10) Patent No.: US 12,082,782 B2
(45) Date of Patent: Sep. 10, 2024

(54) OPTICAL IMAGE STABILIZATION AND ACTIVE ALIGNMENT OF SENSORS IN ENDOSCOPIC CAMERA SYSTEMS AND METHODS OF USING THE SAME

(71) Applicant: KARL STORZ Imaging, Inc., Goleta, CA (US)

(72) Inventor: Christopher Zimmer, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 17/957,401

(22) Filed: Sep. 30, 2022

(65) Prior Publication Data

US 2024/0108204 A1 Apr. 4, 2024

(51) Int. Cl.
*A61B 1/00* (2006.01)
*A61B 1/04* (2006.01)
*A61B 1/05* (2006.01)

(52) U.S. Cl.
CPC ...... *A61B 1/00163* (2013.01); *A61B 1/00096* (2013.01); *A61B 1/042* (2013.01); *A61B 1/051* (2013.01)

(58) Field of Classification Search
CPC ............ A61B 1/00096; A61B 1/00097; A61B 1/00045; A61B 1/042; A61B 1/051; A61B 1/00193; A61B 1/00194
See application file for complete search history.

(56) References Cited

U.S. PATENT DOCUMENTS

| | | | |
|---|---|---|---|
| 5,577,991 A * | 11/1996 | Akui | H04N 13/296 348/45 |
| 2002/0161280 A1* | 10/2002 | Chatenever | A61B 1/042 600/137 |
| 2002/0163581 A1* | 11/2002 | Kitazawa | H04N 23/687 348/208.6 |
| 2003/0076421 A1* | 4/2003 | Dutta | H04N 23/687 348/208.11 |
| 2005/0185057 A1* | 8/2005 | Seo | H04N 23/687 348/208.4 |
| 2006/0126176 A1* | 6/2006 | Nogami | A61B 1/0005 359/464 |

(Continued)

OTHER PUBLICATIONS

Chen, L., and W. Gu, "Imrovement and Optimization of Electromagnetic Integrated Scanning Micromirror," Micromachines, 2021, pp. 1213, v 12(10), MDPI, Basel, Switzerland.

(Continued)

*Primary Examiner* — John P Leubecker
(74) *Attorney, Agent, or Firm* — David N. Villalpando (57) ABSTRACT

Systems and methods are provided that enable optical image stabilization and image sensor alignments. By enabling image sensors to be adjusted based on identified misalignments, users of the systems and methods disclosed herein can adjust imaging during the course of a surgery or surgical procedure, without needing to stop the surgery or surgical procedure to manually realign optical components. The optical image stabilization allows for adjustment of sensor components to compensate for shifts or other movement of imaging devices and to maintain focus on a target object. The optical image stabilization also includes digital masks that can be overlaid on an image to block distracting mask shifting.

8 Claims, 6 Drawing Sheets

(56) References Cited

U.S. PATENT DOCUMENTS

| | | | |
|---|---|---|---|
| 2006/0177208 A1* | 8/2006 | Ito | G03B 17/17 |
| | | | 348/E5.046 |
| 2007/0257989 A1* | 11/2007 | Shirono | H04N 23/68 |
| | | | 348/208.99 |
| 2009/0231418 A1 | 9/2009 | Higuchi | |
| 2010/0063352 A1 | 3/2010 | Matsuura | |
| 2011/0242301 A1* | 10/2011 | Morita | A61B 1/041 |
| | | | 382/128 |
| 2013/0041216 A1* | 2/2013 | McDowall | G02B 6/001 |
| | | | 600/109 |
| 2015/0265143 A1* | 9/2015 | Yoon | A61B 1/0014 |
| | | | 600/104 |
| 2015/0381894 A1* | 12/2015 | Terauchi | H04N 23/54 |
| | | | 348/208.7 |
| 2016/0274350 A1* | 9/2016 | Aizenfeld | H04N 23/51 |
| 2017/0223259 A1* | 8/2017 | Ito | H04N 23/672 |
| 2018/0132706 A1* | 5/2018 | Nagae | A61B 1/00006 |
| 2019/0104239 A1 | 4/2019 | Aschwanden et al. | |
| 2019/0265490 A1* | 8/2019 | Duckett, III | A61B 1/0019 |
| 2019/0391383 A1 | 12/2019 | Duckett, III et al. | |
| 2020/0315432 A1* | 10/2020 | Tully | A61B 1/000094 |
| 2021/0022591 A1 | 1/2021 | Nagae | |
| 2021/0216823 A1 | 7/2021 | Oosake | |
| 2021/0267434 A1* | 9/2021 | Yamaguchi | A61B 1/045 |
| 2023/0209198 A1* | 6/2023 | Lee | H04N 23/57 |
| | | | 348/208.11 |

OTHER PUBLICATIONS

Invitation to Pay Additional Fees and, Where Applicable, Protest Fee for International Application No. PCT/US2023/033925, mailed Jan. 5, 2024.

Thomas, S., International Search Report, Apr. 1, 2024, pp. 1-24, WIPO, Alexandria, USA.

* cited by examiner

OPTICAL IMAGE STABILIZATION AND ACTIVE ALIGNMENT OF SENSORS IN ENDOSCOPIC CAMERA SYSTEMS AND METHODS OF USING THE SAME

BACKGROUND

Endoscopes can be used to provide a visualization of a surgical scene during the course of a surgery or surgical procedure. Video endoscopes or endoscopes used in conjunction with camera heads can provide a video stream of this visualization through the use of associated image sensors. The endoscope and/or an associated camera head often includes optical components, such as beam splitters, filters, and focusing elements, that assist with conditioning light from the surgical scene such that the associated image sensor or sensors are able to generate a video feed of the surgical scene. Image sensors together with a prism assembly comprising one or more beam splitters may form an imaging assembly where the sensors may be directly glued to the beam splitting prism. Due to the sensitive nature of optics, such precision attachment of the sensors to the prism assembly is costly, and any errors in registration can result in an unusable imaging assembly. Further, the mechanical coupling of the beam splitter and the sensor is also susceptible to loss of alignment, such as when an endoscope is bumped, dropped, undergoes mechanical or thermal stress, or is otherwise damaged.

SUMMARY

Issues associated with the above are addressed with systems and methods disclosed herein. By providing an endoscopic camera head, or video endoscope, with sensor modules capable of being registered and adjusted relative to one another, the present disclosure beneficially enables for adjustments of misalignments between the sensors and/or between the sensors and the beam splitter, including during the course of a surgery or surgical procedure, without needing to stop the procedure to correct the misalignment, or to return the misaligned video endoscope or camera head to the manufacturer for replacement or repair.

Additionally, the systems and methods disclosed herein provide for optical image stabilization through detecting endoscope movements, and as a result determining and performing corresponding movement in a sensor to compensate for such movements. As a non-limiting example, a movement of an endoscope may be detected (e.g., with a gyroscope or other orientation/movement detector, such as an accelerometer), and a controller may determine a change in pose (e.g., the position and/or orientation) of an image sensor needed to compensate for the measured movement. The pose of the image sensor may then be adjusted resulting in the video stream generated by endoscope continuously capturing images of a target object. Further, a digital mask smaller than an endoscopic mask may be generated and applied to the displayed video feed, such that movements of the endoscope (and resultant movement of the target object in endoscopic field of view) do not create visual changes on the display. The above may beneficially enable a user of the endoscope to continuously view the target object without seeing a shifting endoscopic mask despite occasional movements of the endoscope. Although this type of misalignment rarely occurs, the present disclosure also beneficially enables adjustment of any misalignments between optical components in the endoscope that might occur during a surgery or surgical procedure, for example due to changes in temperature or humidity, without needing to stop the surgery or surgical procedure to address the misalignment.

DETAILED DESCRIPTION

Embodiments of the present disclosure will be described in connection with components and features of an endoscope. However, to avoid unnecessarily obscuring the present disclosure, the description omits a number of known structures and devices. These omissions are not to be construed as limitations of the scope of the claimed disclosure. Specific details are set forth to provide an understanding of the present disclosure. It should, however, be appreciated that the present disclosure may be practiced in a variety of ways beyond the specific detail set forth herein.

Figure 1:
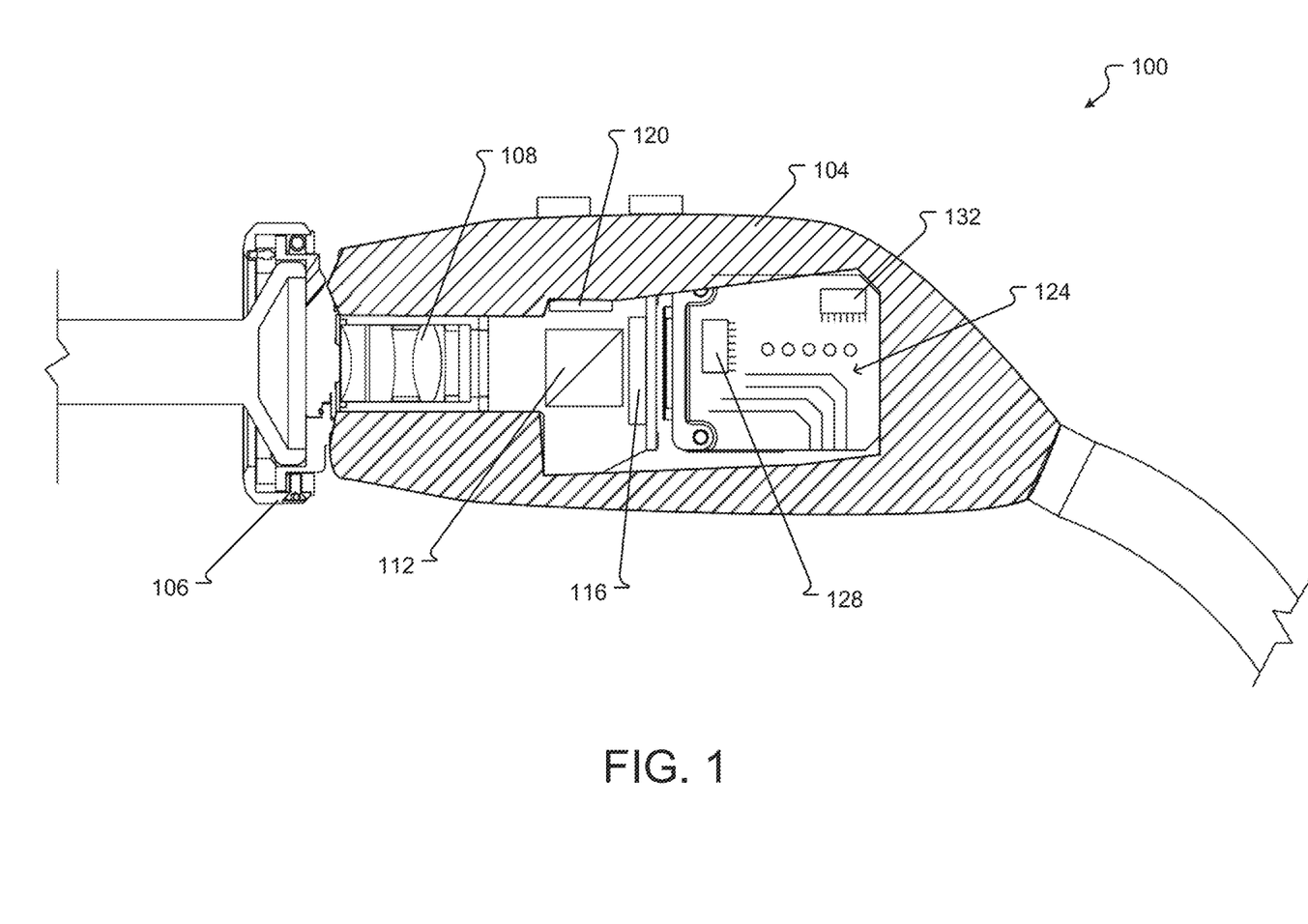
FIG. 1 illustrates an endoscope according to at least one exemplary embodiment.

Turning first to FIG. 1, aspects of an endoscopic camera head 100 are shown in accordance with at least one exemplary embodiment of the present disclosure. It should be noted that this disclosure will generally refer to system 100 as an endoscopic camera head, however, it should be understood that the camera head presented may also be a portion of a single unit endoscope and camera system, usually called a video endoscope, or as a camera head or camera element acting as part of, or attached to, an exoscope. The endoscopic camera head 100 includes a housing 104 within or whereon are housed an optical assembly 108, a prism or prism assembly 112, a first sensor module 116, a second sensor module 120, and processing electronics 124. The processing electronics 124 includes a controller 128 and an orientation/movement detector 132, such as a gyroscope or an accelerometer. The endoscopic camera head 100 also includes a grasping mechanism 106, such as a bayonet connection, disposed on a distal end thereof. In some embodiments, the endoscopic camera head 100 may include additional or alternative components, and the components illustrated in FIG. 1 are in no way limiting. For example, the endoscopic camera head 100 may include additional sensor modules, with the additional sensor modules capable of receiving, for example, different wavelengths, polarizations, magnifications, or intensities of light. In another example, the controller 128 may be disposed externally from the endoscopic camera head 100. In such cases, the controller 128 may communicate with the endoscopic camera head 100 (or components thereof) wirelessly and/or through a wired connection.

The housing 104 may enable storage of one or more hardware components (e.g., cables/wiring, batteries, optical fibers, etc.) that enable one or more additional functions of the endoscopic camera head 100, such as illumination from the distal end of an attached endoscope, video recording of a surgical site, image processing, combinations thereof, and the like.

The grasping mechanism 106 may enable the endoscopic camera head 100 to be connected or attached to one or more other surgical components, usually to a detachable endoscope or components of an exoscope which capture light from a surgical site and relay it to the optical assembly 108 of the endoscopic camera head 100. In some embodiments, the grasping mechanism 106 may include, or allow attachment to, additional optical components, such as spectral filters that filter light entering the optical assembly 108. Additionally optical conditioning adapters or attachments, such as those suggested by Duckett and Kyperountas in U.S. Patent Publication No. 2020/0107710A1 may be attached to the grasping mechanism 106, and an endoscope or exoscope may be further attached thereto. The present disclosure is particularly relevant to such attachments that may result in optical complexities which can be efficiently addressed by the embodiments presented herein.

The optical assembly 108 may be or comprise one or more mirrors, lenses, filters, polarizers, beam splitters, prisms, and/or windows capable of conditioning and/or directing received light to one or more other optical components in the endoscopic camera head 100, such as focusing and directing to the beam splitting prism 112. The optical assembly 108 may be disposed closer to the distal end of the endoscopic camera head 100 than the other optical components, such that the received light passes through the optical assembly 108 before entering the other optical components such as the prism 112. In some embodiments, the optical assembly 108 may be configured to filter, adjust, bend, focus, or otherwise alter the received light based on the type of light received, the type of surgery or surgical procedure in which the endoscopic camera head 100 is used, combinations thereof, and the like. For example, some endoscopes may include a spectral filter in the optical assembly 108 that filters out light of a specific wavelength or a range of wavelengths.

The prism 112 may function as a beam splitter that separates the light received from the optical assembly 108 into two or more light paths. For example, as illustrated in FIG. 1, the prism 112 may separate the received light into two different light paths, with a first light path directed toward the first sensor module 116, and a second light path directed toward the second sensor module 120. In some embodiments, such as an embodiment that includes three separate sensor modules, the prism 112 may be configured to split the received light into three different light paths, with each light path directed toward a different sensor module. The prism 112 may be capable of splitting the received light based on the different wavelengths of the light. In one embodiment, the prism 112 may be able to separate the received light into a white light signal (e.g., light with wavelengths between about 400 nanometers (nm) and about 700 nm) and an infrared (IR) signal (e.g., light with wavelengths above about 800 nm). In this embodiment, the white light signal may be directed into the first sensor module 116, while the IR signal may be directed into the second sensor module 120. This embodiment is particularly useful when performing various types of fluorescence imaging (FI) with a white light overlay. One such application where FI imaging is useful, is in the visualization of the fluorophore indocyanine green (ICG). ICG has an excitation wavelength of about 740-800 nm and emission at 800-860 nm. Therefore, the beam splitting prism 112 can separate the incoming light into a visible band directed towards one sensor and an ICG band directed towards another sensor.

The first sensor module 116 and the second sensor module 120 may be apparatuses that include image sensors (304, see FIG. 3) capable of capturing the light split by the prism 112 and converting the light into an electric signal. The image sensor, such as a CMOS or CCD sensor, includes a plurality of pixels, each containing a photodetector that converts detected light into an electric signal. The number and orientation of the pixels is not limited, and the plurality of pixels may be disposed in, for example, an array. The electric signal may be passed from the first sensor module 116 and/or the second sensor module 120 to the processing electronics 124 and/or the controller 128, where the signal is processed to produce individual images or a video stream. In some embodiments, the image sensors may be capable of processing light with different wavelengths, such as in the ICG FI example discussed above. In one embodiment, the first sensor module 116 may be capable of processing white light or components thereof (e.g., red light, blue light, green light, etc.), and as such, its corresponding image sensor may comprise a Bayer, or other appropriate color filter, while the second sensor module 120 may be capable of processing IR or near-IR light (e.g., light with wavelengths above about 800 nm), and thus its corresponding image sensor may contain no corresponding color filter, increasing, thereby the sensitivity of the second image sensor relative to the first. In embodiments where the endoscopic camera head 100 includes additional sensors, each sensor module may receive and process different wavelengths of light. For example, the white light may be further split into three separate channels of red light, blue light, and green light, with each different color received by a separate image sensor.

In some embodiments, the first sensor module 116 and/or the second sensor module 120 may be mounted on a moveable and/or rotatable platform (e.g., a chassis, a transition stage, etc.) such that the image sensor of the first sensor module 116 and/or that of the second sensor module 120 can be moved relative to the prism 112. As discussed below, the image feed generated by the first sensor module 116 and the second sensor module 120 may be analyzed using one or more feature detection algorithms to detect a misalignment of features in a composite video (e.g., an image or video that is the combination of a first stream generated based on the measurements of the first sensor module 116 and a second stream generated based on measurement of the second sensor module 120). Based on an amount of offset between the detected features, a controller may determine a required adjustment to the first sensor module 116 and/or the second sensor module 120 to resolve the misalignment. The controller may then cause the pose of the image sensor of the first sensor module 116 and/or that of the second sensor module 120 to change to facilitate a re-alignment the first image sensor and/or the second image sensor relative to the prism 112, such that a resultant image produced by a combination of the two image sensors are properly registered with each other.

The controller 128 may communicate with one or more components of the endoscopic camera head 100 (e.g., the first sensor module 116, the second sensor module 120, the processing electronics 124, etc.) to permit the endoscopic camera head 100 and/or components thereof to be controlled or otherwise operated. The controller 128 may cause the movement of the image sensor of the first sensor module 116 and/or the image sensor of the second sensor module 120 to correct misalignments between the first sensor module 116 and/or the second sensor module 120 and the prism 112 that result in a misregistration of the image received by the first sensor module 116 and that received by the second sensor module 120. The controller 128 may also receive and process data received from one or more positional sensors such a gyroscope disposed in the endoscopic camera head 100 or attached endoscope, position sensors disposed within the first sensor module 116 and/or the second sensor module 120, combinations thereof, and the like to appropriately adjust the pose of the respective image sensors of sensor modules 116, 120. As discussed in greater detail below, the controller 128 may use one or more instructions or algorithms to determine a relative movement of the endoscopic camera head 100, and may cause current to flow through electromagnets within the sensor modules 116, 120 to adjust the position of the respective image sensor or within sensor modules 116, 120 to compensate for the movement.

The processing electronics 124 may include one or more electrical components (e.g., resistors, capacitors, transformers, batteries, wiring, cables, etc.) that can be used by the controller 128 to perform one or more functions associated with the endoscopic camera head 100. For example, the processing electronics 124 may provide a power source used by the controller 128 to power a light source in the endoscopic camera head 100. Similarly, the processing electronics 124 may pass current into the first sensor module 116 and/or the second sensor module 120.

The orientation/movement detector 132 may be or comprise an inertial sensor capable of capturing measurements related to acceleration, rotation, or other movement. The orientation/movement detector 132 may communicate with the processing electronics 124 and/or the controller 128. In some embodiments, the measurements generated by the orientation/movement detector 132 may be sent to and used by the controller 128 to determine a magnitude and direction in which the endoscopic camera head 100 has moved. In some embodiments, the endoscopic camera head 100 may include one or more orientation/movement detectors disposed at various locations in the overall endoscopic system, such as near the distal tip of the endoscope as well as within the endoscopic camera head 100, such that the controller 128 can receive multiple readings to determine a more accurate movement change in orientation of the endoscopic camera head 100 (or a component thereof).

Figure 2:
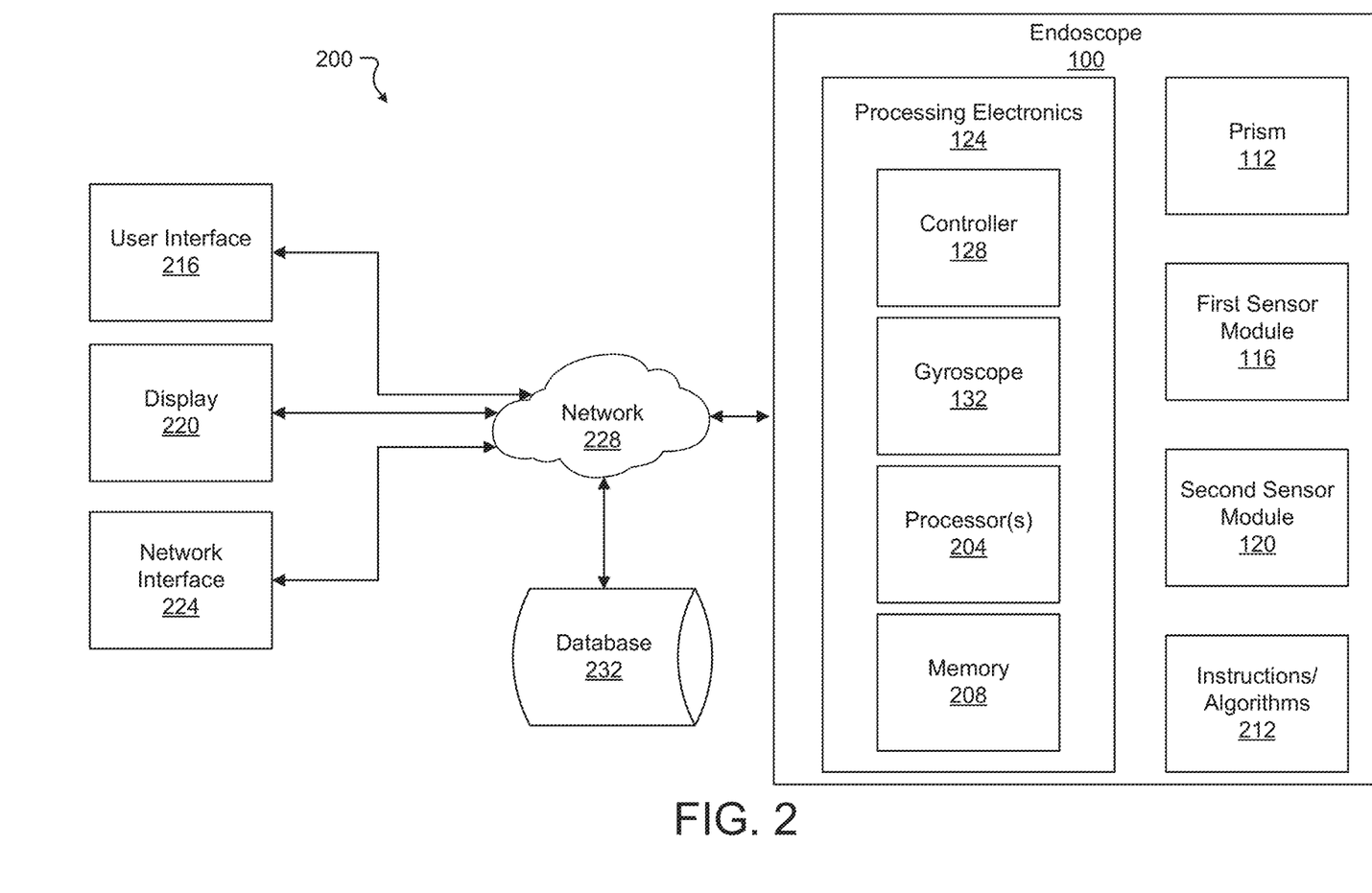
FIG. 2 illustrates a block diagram of a system according to at least one exemplary embodiment.

Turning next to FIG. 2, aspects of a system 200 are shown in accordance with at least one exemplary embodiment. The system 200 includes the endoscopic camera head 100, a user interface 216, a display 220, a network interface 224, a network 228, and a database 232. Notwithstanding the foregoing, the system 200 may include additional or alternative components, and may also omit one or more components shown. In some embodiments, the system 200 may correspond to a processing unit to which the endoscopic camera head 100 is connected. Such an external controller may be comprised in a camera control unit (CCU).

The endoscopic camera head 100 may include the prism or prism assembly 112, the first sensor module 116, the second sensor module 120, and the processing electronics 124 as discussed with respect to FIG. 1. Additionally, the endoscopic camera head 100 may include one or more processors 204, a memory 208, and/or one or more instructions or algorithms 212, or some of these elements may be contained within a CCU connected thereto.

The processor 204 may provide processing functionality and may correspond to one or many computer processing devices. For instance, the processor 204 may be provided as a Field Programmable Gate Array (FPGA), an Application-Specific Integrated Circuit (ASIC), any other type of Integrated Circuit (IC) chip, a collection of IC chips, a microcontroller, a collection of microcontrollers, a GPU(s), or the like. As another example, the processor 204 may be provided as a microprocessor, Central Processing Unit (CPU), Graphics Processing Unit (GPU), and/or plurality of microprocessors that are configured to execute the instructions or algorithms 212 and/or data stored in memory 208. The processor 204 enables various functions of the endoscopic camera head 100 and/or system 200 upon executing the instructions or algorithms 212 and/or data stored in the memory 208.

The memory 208 may be or comprise a computer readable medium including instructions that are executable by the controller 128 and/or the processor 204. The memory 208 may include any type of computer memory device and may be volatile or non-volatile in nature. In some embodiments, the memory 208 may include a plurality of different memory devices. Non-limiting examples of memory 208 include Random Access Memory (RAM), Read Only Memory (ROM), flash memory, Electronically-Erasable Programmable ROM (EEPROM), Dynamic RAM (DRAM), etc. The memory 208 may include instructions that enable the controller 128 to control the various elements of the system 200 and to store data, for example, into the database 232 and retrieve information from the database 232. The memory 208 may be local (e.g., integrated with) the endoscopic camera head 100 or separate from the endoscopic camera head 100.

The instructions 212 comprise computer-readable software that is executable by the controller 128 and/or the processor 204 that cause the controller 128 and/or the processor 204 to perform one or more functions. For example, the instructions 212 may comprise feature detection algorithms (e.g., edge detection algorithms, Harris Corner Detection, Scale-Invariant Feature Transform (SIFT) algorithms, Speeded-Up Robust Features (SURF) algorithms, combinations thereof, etc.) that enable the controller 128 to determine whether there is a misalignment between the prism 112, the first sensor module 116, and/or the second sensor module 120. The controller 128 may process one or more video streams using the feature detection algorithms and determine that there is a misalignment when features present in the video stream created from data generated by the first sensor module 116 do not align with features present in the video stream created from data generated by the second sensor module 120. As an example of the utility of this misalignment detection is clearly evident when the endoscopic camera head 100 is operating in a fluorescence imaging mode, such as when performing ICG fluorescence imaging, where image data from the image sensors of the first sensor module 116 and the second sensor module 120 are used to respectively capture visible and IR light. Since the image sensors of both sensor modules are used to produce a combined image, both image sensors must be correctly aligned with respect to the prism 112 to produce a properly overlayed image.

The user interface 216 includes hardware and/or software that enables user input to the system 200 and/or any one or more components thereof. The user interface 216 may include a keyboard, a mouse, a touch-sensitive pad, touch-sensitive buttons, mechanical buttons, switches, and/or other control elements for providing user input to the endoscopic camera head 100 and/or the system 200 to enable user control over certain functions of the endoscopic camera head 100 and/or the system 200 (e.g., selecting the operating mode, enabling image stabilization, operating lighting and/or imaging capabilities of the endoscopic camera head 100, enabling/permitting compositing of video data streams, rendering processed video to the display 220, etc.). The user interface 216 may include buttons, switches, or other control means disposed on the endoscopic camera head 100 itself independent of or in addition to user interface controls not disposed on the endoscope. Simply as an illustrative example, the endoscopic camera head 100 and/or the display 220 may have input buttons and switches, and, additionally, a keyboard or mouse may be connected directly to the processor 204 (in embodiments where the processor 204 is disposed outside of the endoscopic camera head 100). All of these together constitute the user interface 216.

The display 220 may be or comprise a liquid crystal display (LCD), a light emitting diode (LED) display, a high definition (HD) display, a 4K display, virtual or augmented reality headset, or the like. The display 220 may be a stand-alone display or a display integrated as part of another device, such as a smart phone, a laptop, a tablet, a headset or head-worn device, and/or the like. In one embodiment, the display 220 may be a monitor or other viewing equipment disposed within an operating room, such that video feed captured from a surgery or surgical procedure can be rendered to the display 220 for a physician to view. In some embodiments, the display 220 may comprise a plurality of displays according to, for example, system design.

The network interface 224 may enable one or more components of the system 200 to communicate wired and/or wirelessly with one another or with components outside the system 200. These communication interfaces that permit the components of the system 200 to communicate using the network interface 224 include wired and/or wireless communication interfaces for exchanging data and control signals between one another. Examples of wired communication interfaces/connections include Ethernet connections, HDMI connections, connections that adhere to PCI/PCIe standards and SATA standards, and/or the like. Examples of wireless interfaces/connections include Wi-Fi connections, LTE connections, Bluetooth® connections, NFC connections, and/or the like.

The database 232 includes the same or similar structure as the memory 208 described above. In at least one exemplary embodiment, the database 232 is included in a remote server and stores video data captured during a surgery or surgical procedure (e.g., a camera on an endoscope capturing a live feed during an endoscopy).

Although FIG. 2 illustrates the various elements in the system 200 as being separate from one another, it should be appreciated that some or all of the elements may be integrated with each other if desired. For example, a single desktop or laptop computer may include the processor 204, the memory 208, the user interface 216, and the display 220. It should be further appreciated that each element in the system 200 includes one or more communication interfaces that enable communication with other elements in the system 200 over, for example, the network interface 224. Another example of a preferred embodiment of the system 200 includes an endoscopic camera head 100 with a built in user interface 216 connected to a camera control unit (CCU), the CCU comprising the controller 128, the memory 208, the processor 204, the network interface 224, and a user interface 216, and the CCU is also connected such that it can output image data to the display 220.

Figure 3:
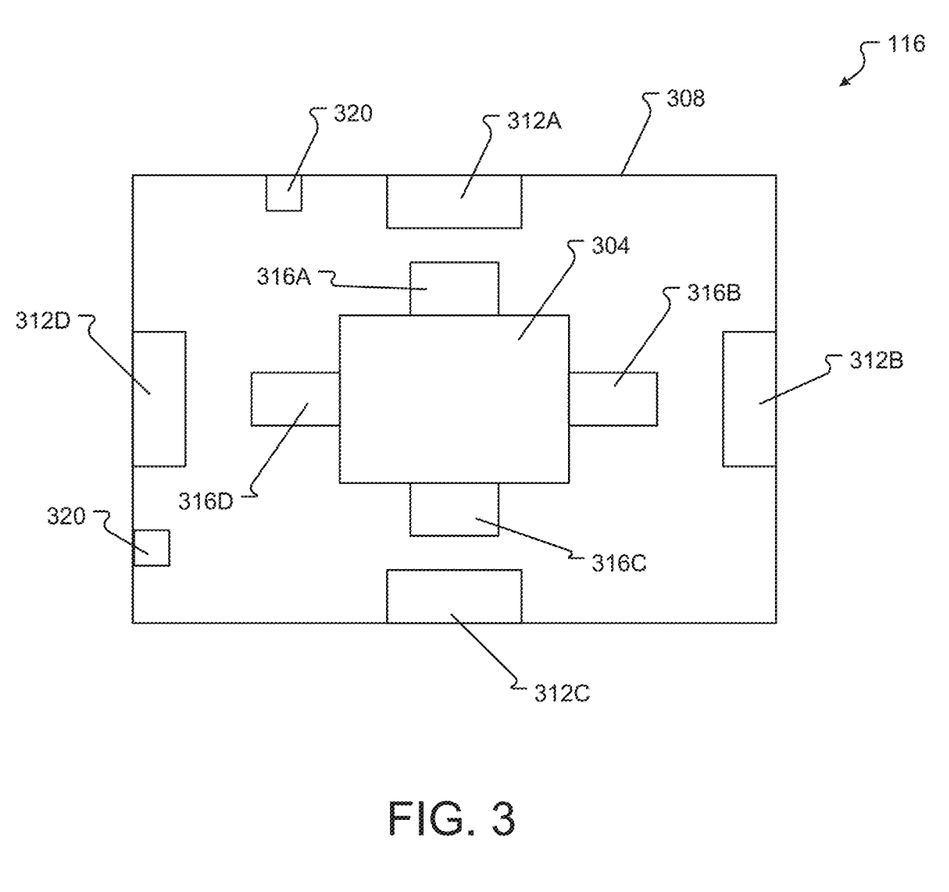
FIG. 3 illustrates a block diagram of a sensor module according to at least one exemplary embodiment.

FIG. 3 shows a block diagram of the first sensor module 116 according to at least one exemplary embodiment of the present disclosure. Additionally or alternatively, the second sensor module 120 may include similar or the same components as those illustrated in FIG. 3. Furthermore, the first sensor module 116 and/or the second sensor module 120 may include additional or alternative components to those depicted in FIG. 3. The first sensor module 116 comprises an image sensor housing 308 that includes an image sensor 304, a plurality of electromagnets 312A-312D, a plurality of sensor magnets 316A-316D, and one or more position sensors 320 that enable the monitoring of the location of the sensor relative to the image sensor module housing.

The image sensor 304 may be configured to capture and convert light into an electric signal. The image sensor, which may be a CMOS or CCD sensor, includes a plurality of pixels, each containing a photodetector that converts detected light into an electric signal. The number and orientation of the pixels is not limited, and the plurality of pixels may be disposed in, for example, and array. The plurality of electromagnets 312A-312D are disposed on inside walls of the image sensor housing 308, and may be capable of receiving a current from a power source, such as a power source disposed outside of the image sensor housing 308 and regulated by the controller 128. The plurality of sensor magnets 316A-316D are generally permanent magnets and are disposed on the image sensor 304, and may hold the image sensor 304 in place relative to the image sensor housing 308 through the electromagnetic interaction between the plurality of electromagnets 312A-312D and the plurality of sensor magnets 316A-316D. The position sensors 320 monitor the position of the image sensor 304 relative to the image sensor housing 308.

The image sensor 304 may be centered within the image sensor housing 308, such that changes in current passing through the plurality of electromagnets 312A-312D causes the plurality of electromagnets 312A-312D to electromagnetically interact with the plurality of sensor magnets 316A-316D. This interaction may generate a force that adjusts the pose of the image sensor 304 within the image sensor housing 308, and thereby its pose relative to the prism assembly 112. The change in current may be generated by the controller 128 when the controller 128 determines that the image sensor 304 should be moved, such as when the controller 128 has determined that the image sensor 304 is not properly positioned relative to the prism 112 and/or with the image sensor in the second sensor module 120. The controller 128 may generate the change in current, which may create a different electromagnetic field in the area of the image sensor 304 as the current passes through the plurality of electromagnets 312A-312D. The changing electromagnetic field may interact with the plurality of sensor magnets 316A-316D attached to the image sensor 304 and cause the image sensor 304 to move (e.g., via translation and/or rotation). In one embodiment, the change in current may cause the image sensor 304 to move orthogonally (e.g., perpendicularly) to an axis normal to an image sensitive surface of the image sensor 304. The resulting movement orthogonal to this axis may cause a change in the resulting image, which may reduce the offset in features of the two video streams. In some embodiments, the position sensors 320 may measure the change in pose of the image sensor 304 and send the measurement to the controller 128. Based on the information provided by the position sensors 320 and the updated information generated by the feature detection algorithm, the controller 128 may determine that additional changes to the pose of the image sensor 304 are needed. In some embodiments, the controller 128 may iteratively adjust the pose of the image sensor 304 until the misalignment is reduced, mitigated, or otherwise eliminated. In some embodiments, the controller 128 may iteratively adjust the pose until the error in registration and/or the difference in the features between the two video streams falls below a threshold value. Once below the threshold value, the controller 128 may treat the image sensor 304 as sufficiently aligned. These positional values may then be stored in the memory 208 for later retrieval if the sensors again become out of alignment. The controller may keep the image sensor 304 in the aligned pose until it is determined that the image sensor 304 is no longer aligned (e.g., when data generated by the position sensor 320 and/or the image received from the first and second image sensor modules are no longer in alignment.

Figure 4A:
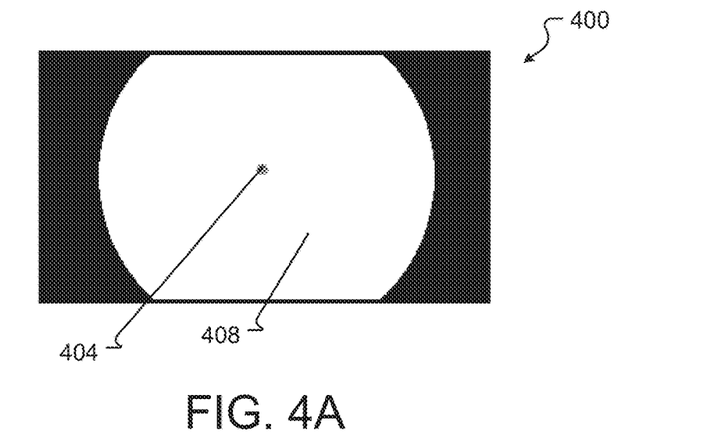
FIG. 4A illustrates a first aspect of optical image stabilization according to at least one exemplary embodiment.
Figure 4B:
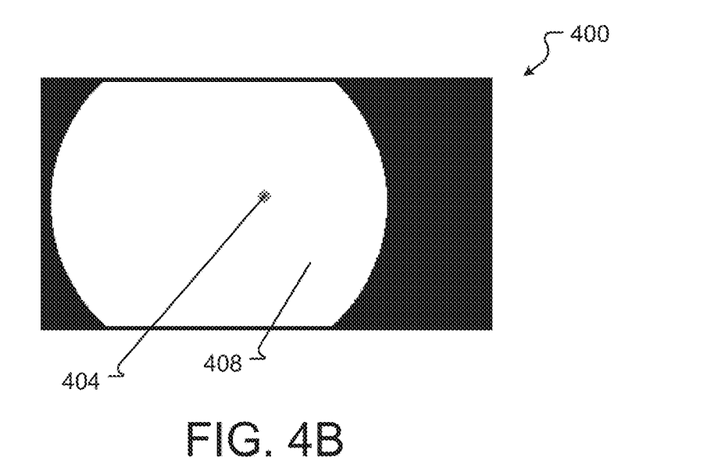
FIG. 4B illustrates a second aspect of optical image stabilization according to at least one exemplary embodiment.
Figure 4C:
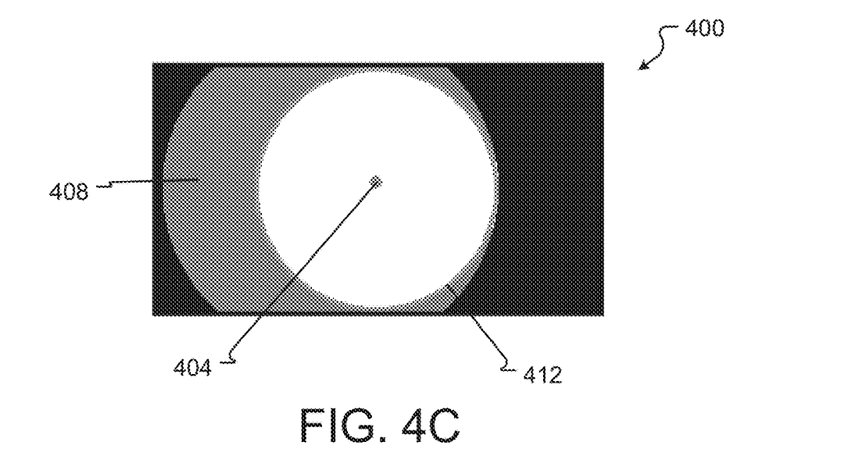
FIG. 4C illustrates a third aspect of optical image stabilization according to at least one exemplary embodiment.

FIGS. 4A-4C illustrate aspects of optical image stabilization according to at least one exemplary embodiment of the present disclosure. The optical image stabilization may be performed by components of the system 200, such as by the controller 128 based on data received from the first sensor module 116, the second sensor module 120, the orientation/movement detector 132, combinations thereof, and the like. Additional or alternative components may be used within the context of the optical image stabilization, and the examples discussed below are in no way limiting to the present disclosure. In some embodiments, the optical image stabilization may be performed when only one of the sensors modules is used (e.g., when only a white light sensor is being used in the endoscopic camera head 100), as misalignment of the two image sensors is not an issue when only one sensor is used for a measurement.

As shown in FIG. 4A, a displayed image 400 may be rendered to a display, such as the display 220. The displayed image 400 may be a singular image based on data received from the first sensor module 116, or may be a video feed, such as a continuous live feed. In such cases, the first sensor module 116 may continuously receive light from the prism 112 and generate electrical signals that are transformed into images by the processing electronics 124 or components thereof by using algorithms contained in the instructions 212. The images are then continuously rendered to the display 220 as the video feed. In the example shown, the displayed image 400 depicts an object 404 (e.g., an anatomical object such as a blood vessel, a tumor, an aspect of the surgical site, etc.) and a first mask 408. The first mask 408 is generally a result (e.g., an artifact) of the optical system, often an image of an aperture contained therein.

As shown in FIG. 4B, a first movement of the endoscope or endoscopic camera head 100 may occur. This movement may be an unanticipated or undesired movement. For example, the endoscopic camera head 100 may move when the physician's hand trembles or accidentally bumps the patient table. The movement may cause the object 404 to move within the field of view of the endoscope. The movement of the endoscopic camera head 100 may be detected and by the orientation/movement detector 132 or image analysis, with the measurement of the movement being passed to the controller 128. The controller 128 then determines a corresponding movement required to compensate for the movement of the endoscopic camera head 100, and cause the first sensor to make a corresponding move enabling the object 404 to remain at its position on the display of the displayed image 400. This can be achieved by the controller 128 adjusting the current flowing into the plurality of electromagnets to cause one or more forces on the sensor to move the sensor, as discussed above.

It should be noted that one of the repercussions of the movement of the image sensor 304 within the first sensor module 116 in order to keep the object 404 properly positioned on the display is a shifting of the first mask 408 relative to the borders of the displayed image 400. In order to compensate for this potentially disorienting shift of the first mask, the controller 128 may generate a second mask 412 that can be overlaid on the displayed image 400, as depicted in FIG. 4C. The second mask 412 may be smaller than the first mask 408 (e.g., the second mask 412 provides for a cropped view of the displayed image 400 than the first mask 408 as shown in FIG. 4B). For example, the second mask 412 may be determined by the controller 128 based on one or more image processing algorithms in the instructions 212 and may be rendered on the display 220 when the controller 128 determines that the object 404 has moved and/or that the first sensor is misaligned. The second mask 412 may, due to the smaller area, prevent the shifting of the first mask 408 on the screen from being rendered to the display 220. In other words, the second mask 412 may allow the user to have a continuous view of the object 404 at its desired position on the displayed image 400 without seeing a potentially distracting shifting of the first mask 408 relative to the endoscopic image 400. The degree to which the second mask 412 is smaller than the first mask 408 may be selected by a user via the user interface 216. Preferences of the size ratio of the first to second masks may be stored in the memory 208, such that multiple surgeons, each with their own preference as to the tradeoff between a narrower field of view and a more stable appearing image, may each store their preferences into the system. Alternatively, the ratio of mask sizes may be automatically selected, or selected from pre-programmed preferences, depending on the type of procedure to be performed, or the type or model of endoscope attached to the endoscopic camera head 100.

For illustrative purposes, the following are two examples of using the endoscopic camera head 100 in accordance with exemplary embodiments of the present disclosure.

In a first example, the endoscopic camera head 100 operates in a fluorescence imaging/white light overlay mode, such as when the endoscopic camera head 100 is configured to capture fluorescence images as well as white light images of an illuminated scene. For example, the endoscopic camera head 100 may operate in an ICG overlay mode and capture near-IR and/or IR light in the emission band of ICG emitted from the fluorophore within the scene, which has been excited by an excitation light source and (either simultaneously or in succession) white light. The excitation and emission spectral bands have been discussed briefly above. Both white light reflected and/or scattered from the tissue along with emitted light from the excited ICG fluorophore are captured by imaging optics, such as the objective lens of an endoscope and relayed to the endoscopic camera head 100. While operating in this mode, the first sensor module 116 may be an RGB sensor, and the second sensor module 120 may be also be an RGB sensor used to capture NIR light, or may be a monochrome NIR sensor. Incoming light passing through the optical assembly 108 may be filtered to remove the excitation light from reaching the prism assembly 112. The prism assembly 112 splits the incoming light based on wavelength bands, directing white light to the first sensor module 116 and NIR light to the second sensor module 120. Data from both sensors are combined to create a false color overlay of the FI image on the white light image of the surgical scene. Alternatively, both the first sensor module 116 and the second sensor module 120 each have a red light channel, a blue light channel, a green light channel, and an IR light channel, which can add versatility to a camera head, but generally at the cost of sensitivity in the NIR channel. To ensure that both the first sensor module 116 and the second sensor module 120 are properly aligned, the first sensor module 116 is registered to the second sensor module 120 and/or to the prism 112, and the second sensor module 120 is mounted in a fixed position relative to the prism 112. Based on the images generated by the first sensor module 116 and the second sensor module 120, the controller 128 can determine that the first sensor module 116 is misaligned relative to the prism 112 and/or the second sensor module 120, and can generate a current that is passed through the first sensor module 116 to move the image sensor 304 in the first sensor module 116 relative to the prism 112. The current can be adjusted iteratively until the image sensor 304 is correctly aligned.

In a second example, the endoscopic camera head 100 operates in a white light mode with image stabilization. In this mode, the illumination source outputs white light without necessarily outputting H excitation light. As a result, only one sensor (e.g., the first sensor module 116) is used to generate images of an illuminated scene, and thus there is no need to align a second sensor with the first sensor. The controller 128 may, in the white light with image stabilization mode, receive measurements from the orientation/movement detector 132 to sense movements in the endoscopic camera head 100 (such as when a surgeon's hand is trembling. The controller 128 then determines, based on the orientation/movement detector 132 measurements, and appropriately moves the image sensor 304 within first sensor module 116 retain a desired field of view on the image display 400. Additionally, the controller 128 may render a smaller mask to shift with the movement of the first sensor module 116, such that the movements of the endoscopic camera head 100 do not create visually disturbing movements of a region of interest rendered to a user display.

Figure 5:
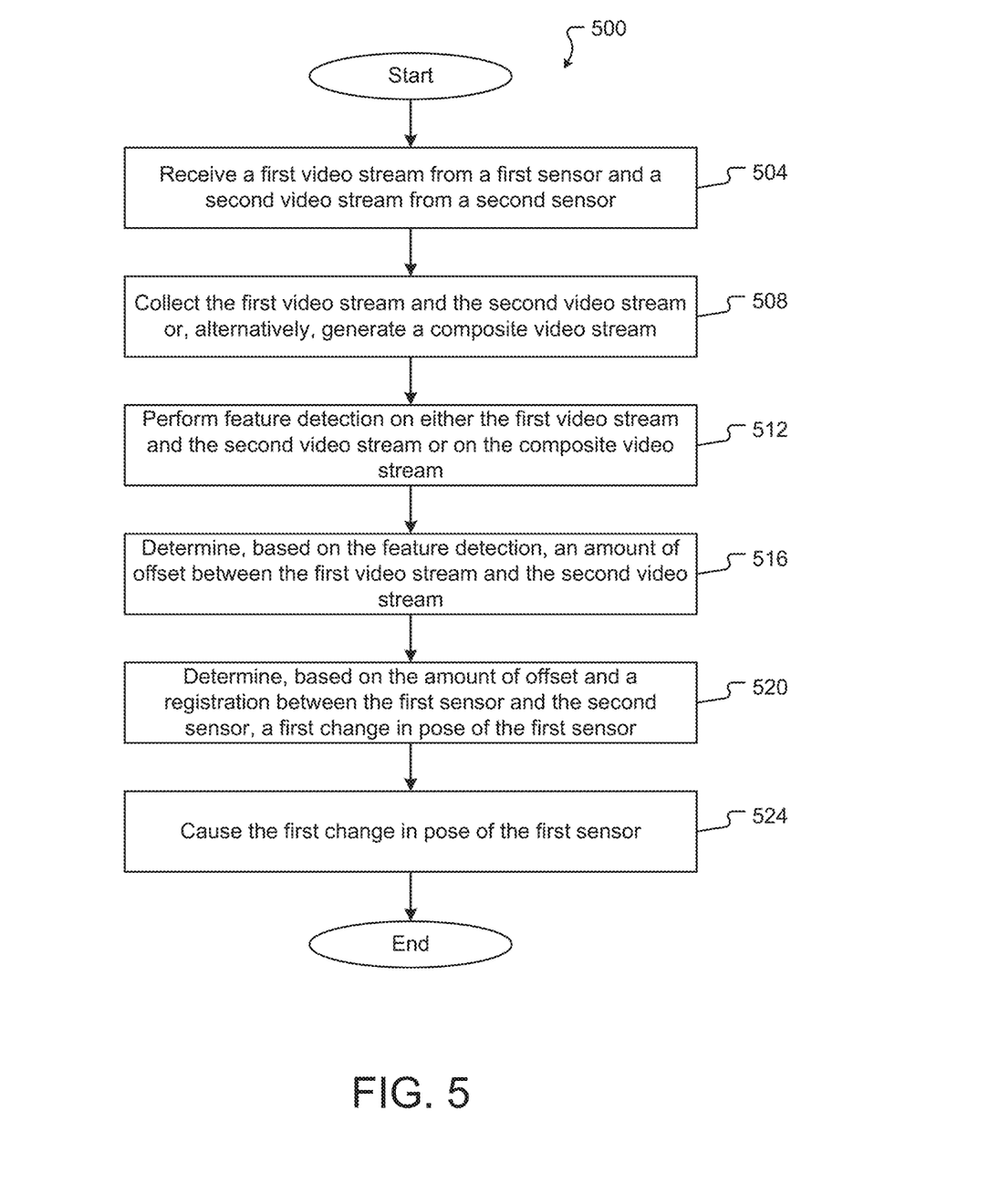
FIG. 5 illustrates a method according to at least one exemplary embodiment.

FIG. 5 illustrates a method 500 according to at least one exemplary embodiment of the present disclosure. The method 500 may be used, for example, to correct a misalignment of image sensors based on a registration of the sensors. In some embodiments, the method 500 may be used when the endoscopic camera head 100 is in a fluorescence imaging mode to correctly align two or more image sensors with the prism 112.

One or more steps of the method 500 may be carried out or otherwise performed, for example, by at least one processor and/or by a controller. The at least one processor may be the same as or similar to the processor 204 of the system 200 as described above. A processor other than any processor described herein may also be used to execute one or more steps of the method 500. The at least one processor may perform one or more steps of the method 500 by executing elements stored in a memory such as the memory 208. The elements stored on the memory 208 (e.g., instructions and/or other data) and executed by the processor 204 may cause the processor 204 to execute one or more steps of the method 500.

The method 500 starts and then proceeds to step 504, where a first video stream from a first sensor and a second video stream from a second sensor are received. The first sensor and the second sensor may be similar to the first sensor module 116 and the second sensor module 120, respectively. The first and second video streams may be generated based on electrical signals generated by the first and second sensors, such as by the controller 128 using processing electronics 124 to create video streams from data received from the first and second sensors.

The method 500 then proceeds to step 508, where the two video streams are collected. Alternately, a composite video stream may be generated based on the first video stream and the second video stream. The composite video stream may be generated by the processing electronics 124 and/or the controller 128 using one or more algorithms included in the instructions 212. The individual video streams and/or the composite video stream may depict one or more features that appear in both the first video stream and the second video stream.

The method 500 then proceeds to step 512, where feature detection is performed on either the individual video streams or the composite video stream. The controller 128 may perform the feature detection using one or more algorithms included in the instructions 212. The method 500 proceeds to step 516 where, based on the results of the feature detection, the controller 128 determines whether there is an offset between the two video streams. The offset between the two video streams may be based on differences in the position or orientation of the detected features, and may indicate that one or more optical components, such as the image sensors, are misaligned. For example, if a first object is centered in the first video stream but appears in the top righthand corner of the second video stream, the controller 128 may determine that the first image sensor and the second image sensor are misaligned.

The method 500 then proceeds to step 520, where the controller 128 determines, based on a registration between the first image sensor and the second image sensor, a first change in pose of the first image sensor to correct the misalignment. The controller 128 may in step 520 use the information related to the offset between the two video streams to determine sets of coordinates associated with the positions of the first and second image sensors, as well as a registration (which may be retrieved, for example, from the database 232) of the two sensors, to calculate a change in pose of the first image sensor. For example, the controller 128 may use a transformation algorithm to transform the offset in the video streams into a first and second sets of coordinates of the first and second image sensors, respectively, and may also determine a third set of coordinates that the first image sensor should be positioned at based on the registration. The controller 128 may then determine the required change in pose to move the first image sensor from the second set of coordinates to the third set of coordinates. The controller 128 may then use one or more algorithms to transform the change in pose into a corresponding current that can be passed to a plurality of electromagnets in the sensor module to move the first image sensor.

The method 500 then proceeds to step 524, where the controller 128 causes the first change in pose of the image sensor. In some embodiments, the controller 128 may generate the current and pass the current through the plurality of electromagnets in the sensor module that include the first image sensor. The current may create an electromagnetic field within the first image sensor module that interacts with magnets connected to the first image sensor. The interaction may generate an electromotive force that causes the first change in pose of the first image sensor. The movement may also be measured by a position sensor (e.g., the position sensors 320) disposed within the first sensor module, with the measurement being passed back to the controller 128. The controller 128 may use the information to iteratively adjust the position of the first image sensor. The method 500 then ends. The method 500 may be exercised whenever there is a question about the proper registration of the two image streams. It may also be exercised as a calibration step as a part of the manufacturing process. The resulting coordinate values that put the first image sensor into proper registration with the second image sensor may be stored on the memory, such that if later, the image sensors come into misalignment due to, for example, mechanical trauma to the instrument, the endoscopic camera head can retrieve these initial, calibrated coordinates, and reapply them, potentially bringing the image sensors back into alignment without the need to re-run method 500. It is also possible to switch, for example, between a white light with image stabilization mode (as described according to FIG. 6) and a white light/FI imaging mode. When returning to a mode where registration between the image sensors is important, the system can retrieve the default coordinates from the memory and apply them, facilitating a reset between modes.

Figure 6:
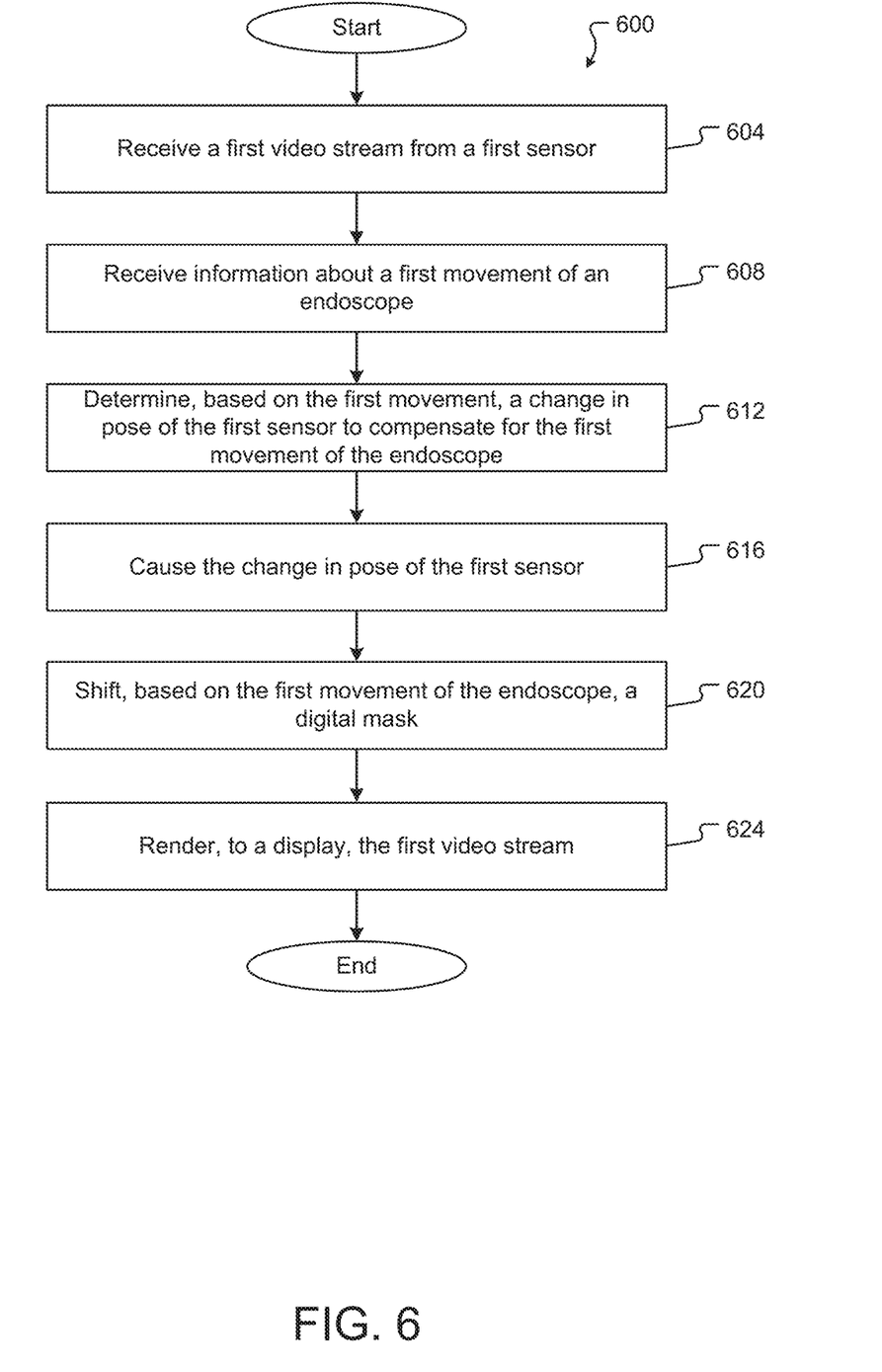
FIG. 6 illustrates a method according to at least one exemplary embodiment.

FIG. 6 illustrates a method 600 according to at least one exemplary embodiment of the present disclosure. The method 600 may be used, for example, to perform optical image stabilization, such as when the endoscopic camera head 100 is operating in a white light only with image stabilization mode.

One or more steps of the method 600 may be carried out or otherwise performed, for example, by at least one processor and/or by a controller. The at least one processor may be the same as or similar to the processor 204 of the system 200 as described above. A processor other than any processor described herein may also be used to execute one or more steps of the method 600. The at least one processor may perform one or more steps of the method 600 by executing elements stored in a memory such as the memory 208. The elements stored on the memory 208 (e.g., instructions and/or other data) and executed by the processor 204 may cause the processor 204 to execute one or more steps of the method 600.

The method 600 starts and proceeds to step 604, where a first video stream from a first sensor is received. The first sensor may be similar to the image sensor 304, and may be associated with the first sensor module 116 or the second sensor module 120, for example. The first video stream may be generated based on the data received from the first sensor.

The method 600 proceeds to step 608 where the controller 128 generates a digital mask and applies it to a first video stream. The digital mask is smaller than an endoscopic mask similar to or the same as the first mask 408, which is a product of the endoscopic or camera head optical system and represents an endoscopic field of view. The digital mask may be similar to or the same as the second mask 412. In other words, the digital mask may be a smaller mask overlaid on the first video stream. The digital mask may be centered on an anatomical element or some other object that is imaged by the endoscope.

The method 600 proceeds to step 612 where information related to a first movement of an endoscope is received. The information may be generated by the orientation/movement detector 132, which records measurements related to the movement of the endoscopic camera head 100. The movement information may be processed by the processing electronics 124 and sent to the controller 128 in step 612, where the controller 128 determines a first change in pose of the first image sensor based on the first movement. The method 600 may then move to step 616, where the controller 128 causes the first change in pose of the first sensor. When the first movement of the endoscope occurs, the view captured by the first video stream may also change, such that the anatomical object moves relative to the first video stream, that is its position shifts within the endoscopic field of view, however, the movement of change of pose of the image sensor in step 612 keeps the anatomical object in the center of the displayed first video stream.

The method 600 proceeds to step 620 where a digital mask shifts due to the first movement of the endoscope. As a result of the shift of the digital mask relative to the endoscopic field of view, a user (e.g., a surgeon, a member of surgical staff, etc.) does not see the movement of endoscopic mask. The method 600 then proceeds to step 624, where the first video stream (including the digital mask) is rendered to a display, such as the display 220. The method 600 then ends.

Although several exemplary embodiments have been described with respect to medical procedures that occur internal to a patient, exemplary embodiments may also be applied to medical procedures that generally occur external to a patient.

An apparatus according to at least one embodiment of the present disclosure comprises: an endoscope, the endoscope comprising: an optical component configured to split light into two or more light paths; a first sensor disposed on a chassis and aligned with a first light path of the two or more light paths; and a second sensor disposed proximate the optical component and aligned with a second light path of the two or more light paths, wherein the first sensor is configured to move relative to at least one of the optical component and the second sensor; and a processor.

Any of the aspects herein, further comprising: a memory storing data thereon that, when processed by the processor, cause the processor to: determine a misalignment between the first sensor and the second sensor; determine, based on a registration between the first sensor and the second sensor, a first change in pose of the first sensor to compensate for misalignment; and cause the first change in pose of the first sensor.

Any of the aspects herein, wherein causing the first change in pose of the first sensor includes causing the first sensor to move orthogonal to an optical axis.

Any of the aspects herein, wherein determining the misalignment includes: receiving a first video stream from the first sensor and a second video stream from the second sensor; and performing feature detection on the first video stream and on the second video stream.

Any of the aspects herein, wherein the processor is further caused to: determine, based on the feature detection, an amount of offset between the first video stream and the second video stream.

Any of the aspects herein, wherein determining the first change in pose of the first sensor to compensate for the misalignment is based at least in part on the amount of offset between the first video stream and the second video stream.

Any of the aspects herein, wherein the first sensor generates a video stream, and wherein data stored on a memory cause the processor to: receive information associated with a movement of the endoscope; determine, based on the information, a movement of the first sensor to compensate for the movement of the endoscope; determine, based on the movement of the endoscope, a change in position of an object depicted in the video stream; shift, based on the movement of the endoscope, a digital mask; and overlay, on the video stream, the digital mask.

Any of the aspects herein, wherein the digital mask is smaller than an endoscopic mask, the endoscopic mask being an artifact of one or more optical elements of an attached endoscope or the apparatus, and wherein a rendering of the video stream on a display does not change when the endoscope moves and the digital mask is overlaid on the video stream.

Any of the aspects herein, wherein the optical component comprises a prism.

Any of the aspects herein, wherein the second sensor is disposed on a second chassis and configured to move relative to at least one of the optical component and the first sensor.

Any of the aspects herein, wherein the endoscope comprises an optical assembly that channels the light into the optical component, and wherein the optical assembly comprises at least one of one or more mirrors, one or more windows, one or more polarizers, one or more lenses, and one or more filters.

Any of the aspects herein, wherein at least one of the first sensor and the second sensor is not mounted to the optical component.

Any of the aspects herein, wherein the first sensor receives white light, and wherein the second sensor receives infrared (IR) light.

Any of the aspects herein, wherein the first sensor is disposed in a sensor module, the sensor module comprising: a plurality of magnets disposed proximate the first sensor; a plurality of electromagnets disposed within an interior of the sensor module; and a position sensor disposed within the interior of the sensor module.

Any of the aspects herein, wherein the processor causes a first change in pose of the first sensor by passing current through the plurality of electromagnets such that an electromagnetic interaction between the plurality of electromagnets and the plurality of magnets causes the first sensor to move.

Any of the aspects herein, wherein the processor causes the first change in pose of the first sensor iteratively, and wherein the current passed through the plurality of electromagnets is adjusted based on a reading from the position sensor.

A method according to at least one embodiment of the present disclosure comprises: receiving light at an endoscope; splitting the light into a first light path and a second light path with an optical component; determining a misalignment between a first sensor and a second sensor, the first sensor disposed on a chassis in the endoscope and aligned with the first light path, and the second sensor disposed proximate the optical component in the endoscope and aligned with the second light path; determining a first change in pose of the first sensor to compensate for the misalignment, the determination made based at least partially on a registration between the first sensor and the second sensor; and causing the first change in pose of the first sensor.

Any of the aspects herein, wherein causing the first change in pose of the first sensor includes causing the first sensor to move orthogonal to an optical axis of the optical component.

Any of the aspects herein, further comprising: receiving a first video stream from the first sensor and a second video stream from the second sensor.

Any of the aspects herein, further comprising: performing feature detection on the first video stream and the second video stream.

Any of the aspects herein, further comprising: generating, based on the first video stream and the second video stream, a composite video stream; and performing feature detection on the composite video stream.

Any of the aspects herein, further comprising: determining, based on the feature detection, an amount of offset between the first video stream and the second video stream.

Any of the aspects herein, wherein determining the first change in pose of the first sensor to compensate for the misalignment is based at least in part on the amount of offset between the first video stream and the second video stream.

Any of the aspects herein, wherein the light received from the endoscope includes an endoscopic mask, and wherein the method further comprises: receiving information associated with a movement of the endoscope; determining, based on the information, a movement of the first sensor to compensate for the movement of the endoscope; determining, based on the movement of the endoscope, a change in position of an object depicted in a video stream; shifting, based on the movement of the endoscope, a digital mask; and overlaying, on the video stream, the digital mask.

Any of the aspects herein, wherein the digital mask is smaller than the endoscopic mask, the endoscopic mask being an artifact of one or more optical elements of the endoscope, and wherein a rendering of the video stream on a display does not change when the endoscope moves and the digital mask is overlaid on the video stream.

Any of the aspects herein, wherein the optical component comprises a prism.

Any of the aspects herein, wherein the second sensor is disposed on a second chassis and configured to move relative to at least one of the optical component and the first sensor.

Any of the aspects herein, wherein the endoscope comprises an optical assembly that channels the light into the optical component, and wherein the optical assembly comprises at least one of one or more mirrors, one or more windows, one or more polarizers, one or more lenses, and one or more filters.

Any of the aspects herein, wherein at least one of the first sensor and the second sensor is not mounted to the optical component.

Any of the aspects herein, wherein the first sensor receives white light, and wherein the second sensor receives infrared (IR) light.

Any of the aspects herein, wherein the first sensor is disposed in a sensor module, the sensor module comprising: a plurality of magnets disposed proximate the first sensor; a plurality of electromagnets disposed within an interior of the sensor module; and a position sensor disposed within the interior of the sensor module.

Any of the aspects herein, wherein causing the first change in pose of the first sensor includes: passing current through the plurality of electromagnets such that an electromagnetic interaction between the plurality of electromagnets and the plurality of magnets causes the first sensor to move.

Any of the aspects herein, wherein causing the first change in pose of the first sensor occurs iteratively, and wherein the current passed through the plurality of electromagnets is adjusted based on a reading from the position sensor.

An apparatus according to at least one embodiment of the present disclosure comprises: an endoscope, the endoscope comprising: an optical component configured to split light into two or more light paths; a first sensor disposed on a chassis and aligned with a first light path of the two or more light paths; and a second sensor disposed proximate the optical component and aligned with a second light path of the two or more light paths, wherein the first sensor is configured to move relative to at least one of the optical component and the second sensor.

Any of the aspects herein, further comprising: a processor; and a memory storing data thereon that, when processed by the processor, cause the processor to: receive a first video stream from the first sensor; receive information about a first movement of the endoscope; determine, based on the first movement, a change in pose of the first sensor to compensate for the first movement of the endoscope; and cause the change in pose of the first sensor.

Any of the aspects herein, wherein the data further cause the processor to: identify an endoscopic mask present in the first video stream; determine, based on the first movement of the endoscope, a change in position of an object depicted in the first video stream; generate, based on the change in position of the object, a digital mask; and overlay, on the first video stream, the digital mask.

Any of the aspects herein, wherein the digital mask is smaller than the endoscopic mask, and wherein the processor is further caused to: render, to a display, the first video stream.

Any of the aspects herein, wherein the position of the object does not move on the display when the endoscope moves and the digital mask is overlaid on the first video stream.

Any of the aspects herein, wherein the first sensor is disposed in a sensor module, the sensor module comprising: a plurality of magnets disposed proximate the first sensor; a plurality of electromagnets disposed within an interior of the sensor module; and a position sensor disposed within the interior of the sensor module.

Any of the aspects herein, wherein a processor causes a change in pose of the first sensor by passing current through the plurality of electromagnets such that an electromagnetic interaction between the plurality of electromagnets and the plurality of magnets causes the first sensor to move.

Any of the aspects herein, wherein the processor causes the change in pose of the first sensor iteratively, and wherein the current passed through the plurality of electromagnets is adjusted based on a reading from the position sensor.

Any aspect in combination with any one or more other aspects,

Any one or more of the features disclosed herein,

Any one or more of the features as substantially disclosed herein,

Any one or more of the features as substantially disclosed herein in combination with any one or more other features as substantially disclosed herein.

Any one of the aspects/features/embodiments in combination with any one or more other aspects/feature/embodiments.

Use of any one or more of the aspects or features disclosed herein.

It is to be appreciated that any feature described herein can be claimed in combination with any other feature(s) as described herein, regardless of whether the features come from the same described embodiment.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

The terms "determine," "calculate," "compute," and variations thereof, as used herein, are used interchangeably and include any type of methodology, process, mathematical operation or technique.

What is claimed is:

1. An apparatus, comprising:
   an endoscope, the endoscope comprising:
      an optical component configured to split light into two or more light paths;
      a first sensor disposed on a chassis and aligned with a first light path of the two or more light paths; and
      a second sensor disposed proximate the optical component and aligned with a second light path of the two or more light paths, wherein the first sensor is configured to move relative to at least one of the optical component and the second sensor, and wherein the movement is orthogonal to an optical axis of the optical component; and
   a processor,
   wherein the first sensor generates a first video stream, and wherein data stored on a memory cause the processor to:
   receive information associated with a movement of the endoscope;
   determine, based on the information, a movement of the first sensor to compensate for the movement of the endoscope;
   determine, based on the movement of the endoscope, a change in position of an object depicted in the first video stream;
   shift, based on the movement of the endoscope, a digital mask; and
   overlay, on the video stream, the digital mask.

2. The apparatus of claim 1, wherein the memory, when processed by the processor, causes the processor to:
   determine a misalignment between the first sensor and the second sensor;
   determine, based on a registration between the first sensor and the second sensor, a first change in pose of the first sensor to compensate for misalignment; and
   cause the first change in pose of the first sensor.

3. The apparatus of claim 2, wherein causing the first change in pose of the first sensor includes causing the first sensor to move orthogonal to the optical axis of the optical component.

4. The apparatus of claim 2, wherein determining the misalignment includes:
    receiving the first video stream from the first sensor and a second video stream from the second sensor; and
    performing feature detection on the first video stream and on the second video stream.

5. The apparatus of claim 4, wherein the processor is further caused to:
    determine, based on the feature detection, an amount of offset between the first video stream and the second video stream.

6. The apparatus of claim 5, wherein determining the first change in pose of the first sensor to compensate for the misalignment is based at least in part on the amount of offset between the first video stream and the second video stream.

7. The apparatus of claim 1, wherein the digital mask is smaller than an endoscopic mask, the endoscopic mask being an artifact of one or more optical elements of an additional attached endoscope or the apparatus, and wherein a rendering of the video stream on a display does not change when the endoscope moves and the digital mask is overlaid on the video stream.

8. The apparatus of claim 1, wherein at least one of the first sensor and the second sensor is not mounted to the optical component.

* * * * *